US008604003B2

(12) United States Patent
Takata et al.

(10) Patent No.: US 8,604,003 B2
(45) Date of Patent: Dec. 10, 2013

(54) PROMOTER FOR HARD TISSUE FORMATION

(75) Inventors: Takashi Takata, Hiroshima (JP); Yuji Kaneda, Tokyo (JP)

(73) Assignee: Seikagaku Corporation, Tokyo (JP)

( * ) Notice: Subject to any disclaimer, the term of this patent is extended or adjusted under 35 U.S.C. 154(b) by 0 days.

(21) Appl. No.: 13/196,713

(22) Filed: Aug. 2, 2011

(65) Prior Publication Data

US 2011/0288048 A1 Nov. 24, 2011

Related U.S. Application Data

(62) Division of application No. 11/908,614, filed as application No. PCT/JP2006/305052 on Mar. 14, 2006, now abandoned.

(30) Foreign Application Priority Data

Mar. 14, 2005 (JP) ................................. 2005-071023
Jun. 16, 2005 (JP) ................................. 2005-176311

(51) Int. Cl.
*A61K 31/727* (2006.01)
(52) U.S. Cl.
USPC ........................................................... 514/56
(58) Field of Classification Search
None
See application file for complete search history.

(56) References Cited

U.S. PATENT DOCUMENTS 6,140,481 A 10/2000 Hara et al.

FOREIGN PATENT DOCUMENTS

| JP | 10-231251 A | 9/1998 |
|---|---|---|
| JP | 2000-212204 A | 8/2000 |
| JP | 2003113090 A | 4/2003 |
| JP | 2003119146 A | 4/2003 |
| JP | 2003-527109 A | 9/2003 |
| JP | 2004-505124 A | 2/2004 |
| JP | 2004-210715 A | 7/2004 |

OTHER PUBLICATIONS

Tsuchiya et al. JP 2003-113090, Apr. 18, 2003, machine translation.*
Noti et al. Chemistry and Biology of Heparin and Heparan Sulfate, H.G. Garg, R.J. Linhardt and C.A. Hales (Editors), 2005, Chapter 4, pp. 79-142.*
Wang et al. J. Clin. Invest. 110:127-136 (2002).*
Mesenchymal Stem cells, http://www.mdsystems.com/molecule_group.aspx?g=805&r=7, downloaded from the internet May 10, 2012.*
Akihisa Saito et al., "Effects of heparin and desulfated heparin on proliferation and differentiation of osteoblastic cells", Mar. 25, 2005, p. 116, vol. 48th Shunki.
Takatora Takada et al., "Heparin enhances the BMP activity", 2004, p. 130, vol. 47th Shunki, Department of Periodontology, Showa University Dental School.
Takatora Takada et al., "Sulfated Polysaccharides Enhance the Biological Activities of Bone Morphogenetic Proteins", The Journal of Biological Chemistry, Oct. 31, 2003, pp. 43229-43235, vol. 278, No. 44, The American Society for Biochemistry and Molecular Biology, Inc., U.S.A.
Tatsuya Koike, "Heparin wa in vivo ni okeru BMP-2 no Kotsuyudo Kassei o Sokushin suru", The Japanese Society for Bone and Mineral Research Program Shorokushu 22nd, 2004, p. 163.
Shunichiro Sato et al., "FGF 2, heparin, dexamethasone, bisphosphonate", Nisshi Hozonshi, 2002, pp. 253-272, vol. 45, No. 2.
Stephanie L. Osip et al., "Differential effects of heparin and low molecular weight heparin on osteoblastogenesis and adipogenesis in vitro", 2004, pp. 803-810, vol. 92, Schattauer GmbH, Stuttgart.
Masaaki Ono et al., "Acceleration of Adipose Conversion of 3T3-L1 Cells by Dextran Sulfate", Biosci. Biotech. Biochem., 1994, vol. 58, No. 5, pp. 934-935, Institute for Biochemical Regulation, School of Agricultural Sciences, Nagoya University, Japan.
F. Blanquaert et al., "Effects of heparin-like polymers associated with growth factors on osteoblast proliferation and phenotype expression", J. Biormed.Mater.Res., 1999, pp. 63-72, vol. 44, John Wiley & Sons, Inc.
Susumu Watanabe et al., "Kotsugasaiboyo Baiyo Saibo ni Taisuru Heparin Tenka no Eikyo", Jinzo, Mar. 21, 1998, pp. 157-160, vol. 21, No. 3.
Misao Nagahata-Ishiguro et al., "Enhancement Action of Sulfated Hyaluronan on the ALPase Activity of Rat Calvarial Osteoblasts", Sen'i Gakkaishi, Apr. 10, 2005, pp. 98-102, vol. 61, No. 4.
Atsushi Irie et al., "Heparan Ryusan wa Kotsukeisei Inshi Signal ni Juyo de aru", Nippon Yakugakkai Nenkai Koen Yoshishu, Mar. 5, 2005, p. 20, vol. 125th, No. 3.

(Continued)

*Primary Examiner* — Layla Bland
(74) *Attorney, Agent, or Firm* — Sughrue Mion, PLLC

(57) ABSTRACT

The present invention provides an agent which induces acceleration of hard tissue formation, acceleration of cell differentiation and increase in cellular alkaline phosphatase activity, by directly acting on the cell. Specifically, it provides a hard tissue formation promoter, a cell differentiation inducer and a cellular alkaline phosphatase activity reinforcing agent comprising, as an active ingredient, a glycosaminoglycan or a salt thereof that keeps sulfate group and has the characteristics of the following (1) and (2): (1) a basic structure is a disaccharide repeating structure consisting of a hexuronic acid residue and a glucosamine residue, (2) one or less of the position among a 2-position hydroxyl group of a hexuronic acid residue, a 6-position hydroxyl group of a glucosamine residue and a 2-position amino group of the glucosamine residue in the basic structure of the aforementioned (1) does not have the sulfate group. In this connection, it is preferable that the hexuronic acid residue is a glucuronic acid residue or an iduronic acid residue.

4 Claims, 9 Drawing Sheets

(56) References Cited

OTHER PUBLICATIONS

Toshie Tsuchiya et al., "Seitai Tekigosei Kinosei ni Sugureta Zairyo to Gijutsu Hyoka no Kaihatsu ni Kansura Kenkyu", Soyaku to Human Science Kenkyu Juten Kenkyu Hokokusho, Heisei 15 Nendo, Dai 6 Bun-ya, Iyo Zairyo oyobi Seizai Sekkei Gijutsu no Kaihatsu nni Kansuru Kenkyu, 2004, pp. 20-28.

Ayumu Ariyoshi et al., "Heparin ni yoru Hakotsusaibo no Bunka oyobi Kotsukyushu Kassei no Seigyo Kiko", J. Oral Biosci., 2004, p. 465, vol. 46, No. 5.

Chieko Hamada et al., "Lipopolysaccharide (LPS) Effect of cytokine on chick osteoclast activity stimulated by lipopolysaccharide and heparin", Juntendo Medical Journal, 1994, pp. 52-60, vol. 40, No. 1.

Marja M. Hurley et al., "Expression and Regulation of Basic Fibroblast Growth Factor mRNA Levels in Mouse Osteoblastic MC3T3-E1 Cells", The Journal of Biological Chemistry, Mar. 25, 1994, pp. 9392-9396, vol. 269, No. 12, U.S.A.

Ryoji Tsuboi et al., Sen'igasaibo Zoshoku Inshi (Heparin Ketsugosei Seicho Inshi), Clinical Immunology, 1990, pp. 1537-1543, vol. 22, No. 10.

S. Sakamoto et al., "Mineralization Induced by B-glycerophosphate in Cultures Leads to a Marked Increase in Collagenase synthesis by Mouse Osteogenic MC3T3-E1 Cells Under Subsequent Stimulation With Heparin", Biochemical and Biophysical Research Communications, Jul. 31, 1989, pp. 773-780, vol. 162, No. 2, Academic Press, Inc.

Akihiko Shiba, "Kisoteki (Shorai) Seikagakuteki Kanten ni Tatta Kotsukyushu to Kotsukeisei (Alkaline Phosphatase o Chushin ni)", The Journal of Dental Medicine, 1984, pp. 753-759, vol. 20, No. 5.

Tsuchiya et al. JP 2003-113090, Apr. 18, 2003, abstract and machine translation.

European Patent Office, Communication dated Jan. 9, 2012 in counterpart European application No. 06729086.

Thomson Scientific, Database WPI, Week 200363, AN 2003-666742, XP 00266643, JP 2003119146 published Apr. 23, 2003.

Thomson Scientific, Database WPI, Week 200367, AN 2003-700685, XP 002666429, JP 2003113090 published Apr. 18, 2003.

Japanese Patent Office, Notification of Reasons for Refusal mailed May 15, 2012 issued in counterpart Japanese Patent Application No. 2007-508162.

\* cited by examiner

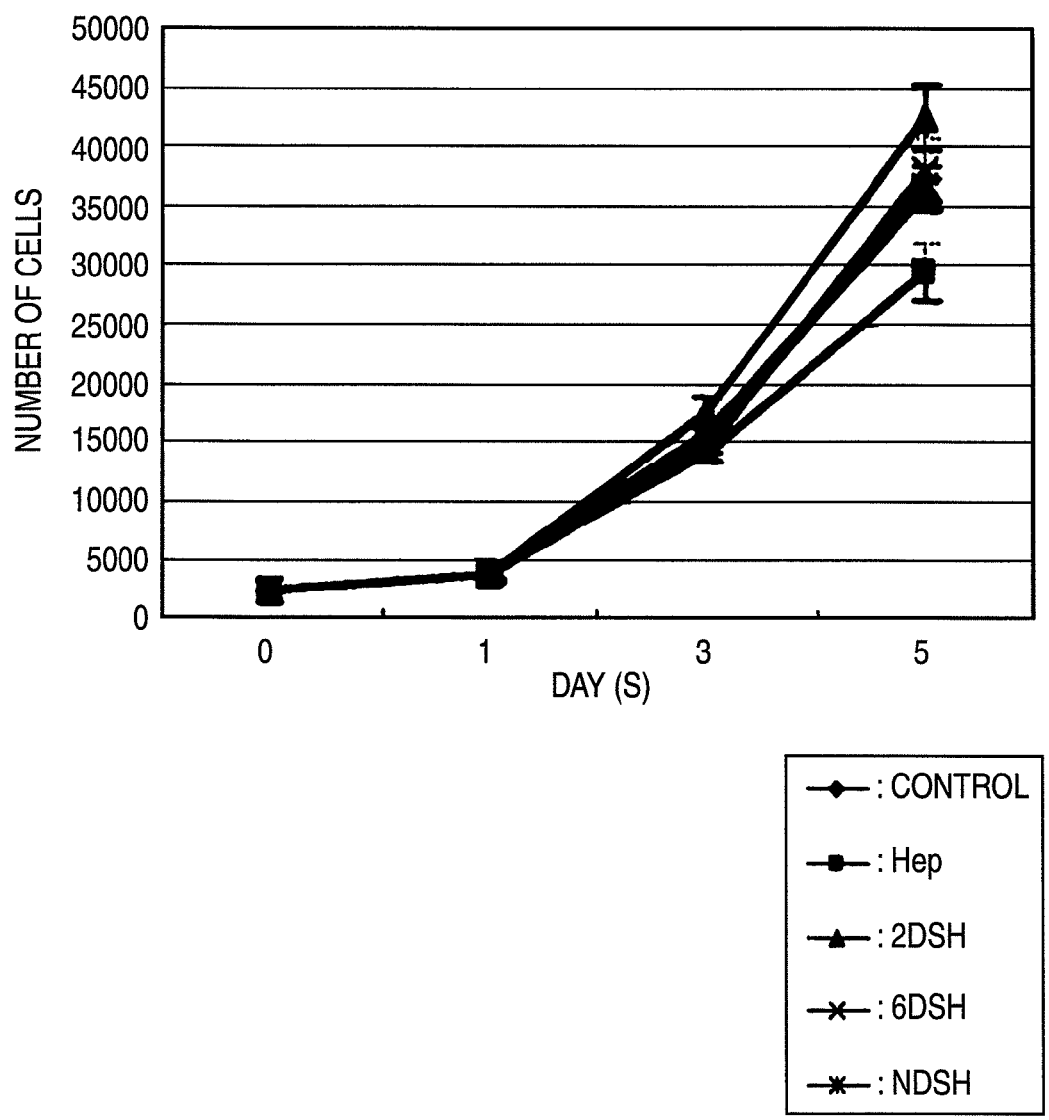

PROMOTER FOR HARD TISSUE FORMATION

This is a Divisional of application Ser. No. 11/908,614 filed Sept. 14, 2007, which is a National Stage of International Application No. PCT/JP2006/305052 filed Mar. 14, 2006, claiming priority based on Japanese Patent Application No. 2005-071023 filed Mar. 14, 2005 and Japanese Patent Application No. 2005-176311 filed Jun. 16, 2005, the contents of all of which are incorporated herein by reference in their entirety.

TECHNICAL FIELD

The present invention relates to a hard tissue formation promoter comprising glycosaminoglycan or a salt thereof, and the like.

BACKGROUND OF THE INVENTION

The following abbreviations are used in the application documents of the present application.
ALP: alkaline phosphatase
αMEM: minimum essential medium alpha medium
BMP-2: bone morphogenetic protein-2
BSP: bone sialoprotein
COLI: type I collagen
FBS: fetal bovine serum
GAG: glycosaminoglycan
GlcN: glucosamine
GlcA: glucuronic acid
Hep: heparin
HexA: hexuronic acid
HS: heparan sulfate
IdoA: iduronic acid
PCR: polymerase chain reaction
RT-PCR: reverse transcription PCR
2DSH: 2-O-desulfated Hep (2-O-desulfated heparin) (a substance in which a 2-position hydroxyl group of HexA residue in Hep is desulfated)
6DSH: 6-O-desulfated Hep (6-O-desulfated heparin) (a substance in which a 6-position hydroxyl group of GlcN residue in Hep is desulfated)
NDSH: N-desulfated Hep (N-desulfated heparin) (a substance in which a 2-position amino group of GlcN residue in Hep is desulfated)

Background art of the present invention is described in the following.

In Patent Reference 1, an intercellular connection promoter comprising, as the active ingredient, GAG which has a sulfate and a disaccharide repeating structure consisting of a HexA residue and a GlcN residue as the basic structure, wherein said GAG comprises the HexA residue in which a 2-position hydroxyl group is not esterificated with sulfuric acid or the GlcN residue in which a 2-position amino group is not sulfaminated is described.

In Patent Reference 2, an intercellular connection suppressor comprising, as the active ingredient, GAG which has a sulfate group and a disaccharide repeating structure consisting of a HexA residue and a GlcN residue as the basic structure, wherein said GAG contains the Glc residue in which a 6-position hydroxyl group is not esterificated with sulfuric acid is described.

Patent Reference 3 discloses a certain species of desulfated Hep, and discloses an accelerator of a basic fibroblast growth factor activity comprising the same as an active ingredient and a composition which comprises the same and the basic fibroblast growth factor and accelerates activity of the basic fibroblast growth factor upon the cell growth.

Patent Reference 4 discloses a hyaluronic acid fraction having a bone formation activity and a molecular weight of from 20 kDa to 40 kDa.
Patent Reference 1: JP-A-2003-113090
Patent Reference 2: JP-A-2003-119146
Patent Reference 3: International Publication No. 96/01278
Patent Reference 4: Japanese Patent No. 3333205

However, there is no disclosure or suggestion that a GAG or a salt thereof, which has a sulfate group and a disaccharide repeating structure consisting of a HexA residue and a GlcN residue as a basic structure, wherein one or less of the position among a 2-position hydroxyl group of the HexA residue, a 6-position hydroxyl group of the GlcN residue and a 2-position amino group of the GlcN residue in the basic structure does not have the sulfate group, by itself has activity of directly accelerating hard tissue formation, accelerating differentiation of a cell and increasing ALP activity of the cell.

DISCLOSURE OF THE INVENTION

Problems to be Solved by the Invention

The object of the present invention is providing an agent which induces acceleration of hard tissue formation, acceleration of cell differentiation and increase in ALP activity of a cell, by directly acting on the cell.

Means for Solving the Problems

To solve the aforementioned problems, the inventors of the present invention have conducted intensive studies and found as a result that a certain species of GAG or a salt thereof induces acceleration of hard tissue formation, acceleration of cell differentiation and increase in ALP activity of a cell, by directly acting upon the cell. As a result, the present invention was accomplished.

Accordingly, the present invention provides a hard tissue forming agent comprising, as an active ingredient, a GAG or a salt thereof that has a sulfate group and the characteristics of the following (1) and (2) (to be referred to as "forming promoter of the present invention" hereinafter):

(1) a basic structure is a disaccharide repeating structure consisting of a HexA residue and a GlcN residue,
(2) one or less of the position among a 2-position hydroxyl group of the HexA residue, a 6-position hydroxyl group of the GlcN residue and a 2-position amino group of the GlcN residue in the basic structure of the aforementioned (1) does not have the sulfate group.

It is preferable that the HexA residue is a GlcA residue or an IdoA residue. Also, as the GAG which has the sulfate group and the aforementioned characteristics, 1 or 2 or more substances selected from the group consisting of Hep, a substance which does not have the sulfate group on the 2-position hydroxyl group of HexA residue of Hep, a substance which does not have the sulfate group on the 6-position hydroxyl group of GlcN residue of Hep and a substance which does not have the sulfate group on the 2-position amino group of GlcN residue of Hep. Additionally, it is desirable that the hard tissue is a bone.

Also, the present invention provides a cell differentiation promoter comprising, as an active ingredient, a GAG or a salt thereof that has a sulfate group and the characteristics of the following (1) and (2) (to be referred to as "differentiation promoter of the present invention" hereinafter):

(1) a basic structure is a disaccharide repeating structure consisting of a HexA residue and a GlcN residue, (2) one or less of the position among a 2-position hydroxyl group of the HexA residue, a 6-position hydroxyl group of the GlcN residue and a 2-position amino group of the GlcN residue in the basic structure of the aforementioned (1) does not have the sulfate group.

It is preferable that the HexA residue is a GlcA residue or an IdoA residue. Also, as the GAG which has sulfate group and the aforementioned characteristics, 1 or 2 or more substances selected from the group consisting of a Hep, a substance which does not have the sulfate group on a 2-position hydroxyl group of the HexA residue of the Hep, a substance which does not have the sulfate group on a 6-position, hydroxyl group of the GlcN residue of the Hep and a substance which does not have the sulfate group on the 2-position amino group of the GlcN residue of the Hep is specifically preferable. Additionally, it is preferable that the cell is a bone marrow-derived mesenchymal cell or an osteoblast.

Also, the present invention provides a cellular ALP activity reinforcing agent comprising, as an active ingredient, a GAG or a salt thereof that has a sulfate group and the characteristics of the following (1) and (2) (to be referred to as "activity reinforcing agent of the present invention" hereinafter):

(1) a basic structure is a disaccharide repeating structure consisting of a HexA residue and a GlcN residue, (2) one or less of the position among a 2-position hydroxyl group of the HexA residue, a 6-position hydroxyl group of the GlcN residue and the 2-position amino group of the GlcN residue in the basic structure of the aforementioned (1) does not have the sulfate group.

It is preferable that the HexA residue is a GlcA residue or an IdoA residue. Also, as the GAG which has the sulfate group and the aforementioned characteristics, 1 or 2 or more substances selected from a group consisting of a Hep, a substance which does not have sulfate group on a 2-position hydroxyl group of the HexA residue of the Hep, a substance which does not have the sulfate group on a 6-position hydroxyl group of the GlcN residue of the Hep and a substance which does not have the sulfate group on a 2-position amino group of the GlcN residue of the Hep is specifically preferable. Additionally, it is preferable that the cell is a bone marrow-derived mesenchymal cell or an osteoblast.

Hereinafter, the forming promoter of the present invention, differentiation promoter of the present invention and activity reinforcing agent of the present invention are called "agent of the present invention" as a whole.

Effect of the Invention

The agent of the present invention is markedly useful, since the GAG which is the active ingredient exerts superior effect by directly acting on the hard tissue formation, cell differentiation acceleration or cellular ALP activity increase.

BEST MODE FOR CARRYING OUT THE INVENTION

The following describes the present invention in detail based on the best mode for carrying out the present invention.
<1> Active Ingredient of the Agent of the Present Invention The agent of the present invention comprising as an active ingredient, a GAG or a salt thereof that has sulfate group and the characteristics of the following (1) and (2):

(1) a basic structure is a disaccharide repeating structure consisting of a HexA residue and a GlcN residue, (2) one or less of the position among a 2-position hydroxyl group of the HexA residue, a 6-position hydroxyl group of the GlcN residue and the 2-position amino group of the GlcN residue in the basic structure of the aforementioned (1) does not have the sulfate group.

In this case, although the HexA residue is not particularly limited, it is preferable that the Hex A residue is a GlcA residue or an IdoA residue. Particularly, it is preferable that the GlcA residue is a D-GlcA residue and it is preferable that the IdoA residue is a L-IdoA residue. Also, although the GlcN residue is not particularly limited, it is preferable that the GlcN residue is a D-GlcN residue.

Additionally, amino group of the GlcN residue may be acetylated. In that case, the moiety of the GlcN residue becomes N-acetylglucosamine (GlcNAc).

The basic structure of the GAG as the active ingredient of the agent of the present invention is a disaccharide repeating structure consisting of such HexA residue and GlcN residue. Namely, when the HexA residue is regarded as "a", and the GlcN residue as "b", the GAG as the active ingredient of the agent of the present invention consists of a basic structure of "a-b-a-b- . . . " or "b-a-b-a- . . . ". In this connection, the "-" represents glycosidic linkage. When "a" is GlcA residue, it is preferable that the glycosidic linkage between "a" and "b" (a-b) is β1→4 linkage. Also, when "a" is the IdoA residue, it is preferable that the glycosidic linkage between "a" and "b" (a-b) is α1→4 linkage. Additionally, it is preferable that the glycosidic linkage between "b" and "a" (b-a) is α1→4 linkage.

Such a GAG as the active ingredient of the agent of the present invention comprises a sulfate group. Although the position which has the sulfate group in the aforementioned basic structure is not particularly limited, at least 1 position selected from a 2-position hydroxyl group of the HexA residue, a 6-position hydroxyl group of the GlcN residue and a 2-position amino group of the GlcN residue is preferable. Examples of the GAG which has the sulfate group at such a position include Hep and HS, for example.

However, in order to use it as the active ingredient of the agent of the present invention, it is necessary 1 or less of the positions among the 2-position hydroxyl group of the HexA residue, the 6-position hydroxyl group of the GlcN residue and the 2-position amino group of the GlcN residue in the aforementioned basic structure does not have the sulfate group. Accordingly, examples of the active ingredient of the agent of the present invention include a Hep (all of the 2-position hydroxyl group of HexA residue, the 6-position hydroxyl group of the GlcN residue and the 2-position amino group of the GlcN residue have the sulfate group), 2DSH, 6DSH, NDSH and the like.

In this connection, GAG is a polysaccharide (polymer), and it does not have to say that it is a technical common sense of said technical field that the complete sameness of the size of molecule, composition and sequences of the constituting sugars, position of the sulfate group, the number of the sulfate groups, and the like, is substantially impossible. Additionally, it is also a technical common sense of said technical field that, for example, when it is said that "the 2-position hydroxy group of the HexA residues does not have the sulfate group" in such a GAG, it does not mean that "the 2-position hydroxy groups of all of the HexA residues in the GAG molecule do not have the sulfate group completely", but means that "it is sufficient when the majority of the 2-position hydroxy groups of HexA residues in the GAG molecule do not have the sulfate group, so that a case in which some 2-position hydroxy groups of HexA residues have the sulfate group is not excluded". Thus, these descriptions in the application documents of the instant application are also should be understood in accordance with the technical common sense in said technical field.

It is necessary that 1 or less of the positions among the 2-position hydroxyl group of the HexA residue, the 6-position hydroxyl group of the GlcN residue and the 2-position amino group of the GlcN residue in the aforementioned basic structure do not have the sulfate group.

The origin of GAG as the active ingredient of the agent of the present invention is not limited too. A natural product may be used as such; a natural product may further processed by chemical methods, enzymatic methods or other methods, or a chemically synthesized substance may be used.

For example, when a Hep is used as the active ingredient of the agent of the present invention, a Hep obtained from a natural product or the like by a conventionally known method may be used as such, or a Hep which is already on the market as a pharmaceutical preparation or a reagent may be used. Alternatively, a substance in which the degree of sulfation of HS is increased to a similar level of Hep by conventionally known chemical methods, enzymatic methods or other methods may be used. The term "Hep" in the application documents of the present application includes not only a pure and simple Hep but also such a substance which can be recognized as substantially the same as the Hep.

Additionally, also in the case where 2DSH, 6DSH or NDSH as the active ingredient of the agent of the present invention are used, it can be produced by the method described in the aforementioned Patent Reference 1 and Patent Reference 2.

Size (weight average molecular weight) of the GAG which can be used as the active ingredient of the agent of the present invention is not particularly limited, as long as it can be recognized as a "polysaccharide" by those skilled in the art in the technical field. For example, its weight average molecular weight is preferably from about 5,000 to 20,000, more preferably from about 10,000 to 15,000. In this connection, the weight average molecular weight can be measured in accordance with the method described in WO 00/06608.

Also, purity of the GAG which is used as the active ingredient of the agent of the present invention is not particularly limited too, and can be appropriately selected according to the case, object and the like of applying the agent of the present invention.

For example, when the agent of the present invention is applied to objects which require high degree sterility, cleanness and the like such as a tissue in the living body, a cell cultured under an aseptic condition and the like, it is preferable to use a substance which is highly purified and substantially does not include medically and culturally unacceptable materials such as endotoxin, microorganisms and the like. Additionally, when the agent of the present invention is applied to an object which does not require high degree sterility, cleanness and the like to that extent, the purification degree may be appropriately reduced in response to the case and object.

Also, the "salt of GAG" is not particularly limited too, and can be appropriately selected according to the case, object and the like of applying the agent of the present invention. For example, when it is applied to a tissue in the living body, a medically acceptable salt may be selected. As the salt of GAG, for example, an alkali metal salt (sodium salt, lithium salt, potassium salt or the like), an alkaline earth metal salt, salts with inorganic bases such as an ammonium salt and the like, or salts with organic bases and the like such as a diethanolamine salt, a cyclohexylamine salt, an amino acid salts and the like can be exemplified. A sodium salt is particularly preferable.

The agent of the present invention may contain one species of the aforementioned GAG or a salt thereof alone as the active ingredient, or may contain two or more species of the aforementioned GAG or salts thereof as the active ingredient.

By using such a GAG or a salt thereof, preparation of a forming promoter of the present invention, a differentiation promoter of the present invention and an activity reinforcing agent of the present invention, which has markedly excellent effects is possible.

<2> Dosage Forms and the Like of the Agent of the Present Invention

Dosage forms and the like of the agent of the present invention are not particularly limited, as long as they contain the aforementioned GAG or a salt thereof, and the acceleration activity of hard tissue formation, acceleration activity of cell differentiation and reinforcing activity of ALP activity of a cell are exerted by it. They can be appropriately selected according to the case, object and the like of applying the agent of the present invention.

For example, the agent of the present invention may be made into an agent of a solution state containing the aforementioned GAG or solid preparations of a salt thereof, or into powders, granules and the like. Alternatively, for example, when it is provided as a solution state agent, it may be provided under a frozen state; provided as the solution as such; or provided as an agent which is dissolved prior to its use.

Concentration of the aforementioned GAG or a salt thereof in the agent of the present invention is not particularly limited too, and can be appropriately selected according to the case, object and the like of applying the agent of the present invention.

Preparation of the Agent of the Present Invention into Pharmaceutical preparations can be carried out by conventionally known methods. Additionally, components for removing other agent and a stabilizer, an emulsifying agent, an adjusting agent of osmotic pressure, a buffer agent, a tonicity agent, a corrective, a preservative, a pH adjusting agent, a soothing agent, a coloring agent, an excipient, a binder, a lubricant, a disintegrating agent and the like other components can be formulated in preparing the pharmaceutical preparations, as long as they do not have a bad influence upon the aforementioned GAG or a salt thereof and also do not exert influence upon the effect of the present invention.

<3> Use, Using Method and the Like of the Agent of the Present Invention

The agent of the present invention can be made into a hard tissue formation promoter, a cell differentiation promoter or a cell ALP activity reinforcing agent. When it is made into a hard tissue formation promoter (formation promoter of the present invention), it is preferable that the "hard tissue" is a bone. In this connection, the "acceleration of hard tissue formation" includes a meaning of accelerating calcification. Also, when it is made into a cell differentiation promoter (differentiation promoter of the present invention) or a cell ALP activity reinforcing agent (activity reinforcing agent of the present invention), it is preferable that the "cell" is a bone marrow-derived mesenchymal cell or an osteoblast. Additionally, the agent of the present invention may be made into a single agent at one of these uses or a single agent aiming at two or more of these uses.

Administration and application methods of the agent of the present invention are not limited, as long as the aforementioned GAG or a salt thereof which is used as its active ingredient is under such a condition that it can contact with an object to be applied such as a living body tissue, cell or the like.

The agent of the present invention can be used as a medicament, a reagent and the like aiming, for example, at accelerating hard tissue formation, accelerating cell differentiation or reinforcing cell ALP activity. When the agent of the present invention is used as a medicament, its dose should be individually set depending on the purpose of the administration (prevention, maintenance (prevention of deterioration), alleviation (improvement of symptoms) or treatment), kind of the disease, symptom, sex, age and body weight of the patient, administration region, administration method and the like. Although it is not particularly limited, in general, approximately from 0.03 mg/administration region to 3 mg/administration region per once per adult can be administered as the aforementioned GAG or a salt thereof.

When the agent of the present invention is made into a medicament, although the animal to which it is administered is not particularly limited too, a vertebrate is preferable; a mammal is more preferable; and human is particularly preferable. In this case, it can be administered for example to the following animals, according to each use.

When it is used as a hard tissue formation promoter, it can be administered to an animal which is under a condition that acceleration of the formation of a hard tissue is required. Examples of such a condition include a case of suffering from bone fracture, bone damage, osteoporosis or the like, a condition of just after the application of a dental treatment, an orthopedic treatment, bone prosthesis or the like, and the like.

When it is used as a cell differentiation promoter, it can be administered to an animal which is under such a condition that differentiation of cells is required. Particularly, it is desirable to administer it to an animal which is under a condition that differentiation of a bone marrow-derived mesenchymal cell, an osteoblast or the like is required. Examples of the condition in which differentiation of such a cell is required are the same as the case of the aforementioned hard tissue formation promoter.

When it is used as a cell ALP activity reinforcing agent, it can be administered to an animal which is under a condition that increase in ALP activity in cells is required. Examples of such a condition are the same as the case of the aforementioned hard tissue formation promoter and cell differentiation promoter.

When the agent of the present invention is used as a reagent, although its application object is not particularly limited too, examples of the object includes a tissue collected from a living body, a cultured cell and the like.

Additionally, the aforementioned GAG or a salt thereof as the active ingredient of the agent of the present invention may be used as a raw material with the aim of accelerating hard tissue formation, accelerating cell differentiation or reinforcing ALP activity in cells, by immobilizing it on the surface of an appropriate insoluble carrier or mixing it with an appropriate raw material. As such an insoluble carrier (raw material), those which have various shapes, such as beads, film, plate, monofilament, non-woven fabric, sponge, cloth, knitting, staple fiber, tube, hollow fiber, hydroxyapatite and the like, can be used. Specifically, it can be used in an implant, bone cement, a bone prosthetic agent, a root canal filler, a bone plate, an artificial joint and the like as medical composite materials. Additionally, the agent of the present invention can also be applied as a raw material in the field of regeneration medical treatment.

EXAMPLES

The present invention is specifically explained in detail based on examples as follows:

<1> Materials

The materials used in the examples are described below.

1. Cell Strains

A mouse bone marrow-derived mesenchymal cell strain, ST2 cell strain, and a mouse osteoblast-like cell strain having more high differentiation degree, MC3T3-E1 cell strain, (both obtained from RIKEN CELL BANK), were used. In the following, culturing of these cells was carried out all under a condition of 37° C. and 5% $CO_2$. Additionally, antibiotics (100 U/ml in final concentration of penicillin G, 100 μg/ml in final concentration of streptomycin and 250 μg/ml in final concentration of gentamicin) were allowed to coexist in all of the media to be used for the culturing of these cells.

2. Samples to be Tested

The followings were used as the samples to be tested. All of the samples provided by Seikagaku Corporation were used. In this connection, the abbreviations in parentheses mean those shown in FIG. 1.

Hyaluronic acid having a weight average molecular weight of 10,000 (hyaluronic acid 10,000)

Hyaluronic acid having a weight average molecular weight of 60,000 (hyaluronic acid 60,000)

Hyaluronic acid having a weight average molecular weight of 350,000 (hyaluronic acid 350,000)

Hyaluronic acid having a weight average molecular weight of 1,000,000 (hyaluronic acid 1,000,000)

Hyaluronic acid having a weight average molecular weight of 1,500,000 (hyaluronic acid 1,500,000)

Hyaluronic acid having a weight average molecular weight of 2,500,000 (hyaluronic acid 2,500,000)

Hep

2DSH

6DSH

NDSH

NSH (a substance in which the 2-position amino group of the GlcN residue in the Hep is sulfated, and the 2-position hydroxyl group of the HexA residue and the 6-position hydroxyl group of the GlcN residue do not have the sulfate group)

6SH (6-O-sulfated Hep; 6-O-sulfated heparin; a substance in which the 6-position hydroxyl group of the GlcN residue is sulfated, and the 2-position hydroxyl group of the HexA residue and the 2-position amino group of the GlcN residue do not have the sulfate group)

2SH (2-O-sulfated Hep; 2-O-sulfated heparin; a substance in which the 2-position hydroxyl group of the HexA residue in the Hep is sulfated, and the 6-position hydroxyl group of the GlcN residue and the 2-position amino group of the GlcN residue do not have the sulfate group)

DSH (desulfated Hep; desulfated heparin; a substance in which the Hep was completely desulfated)

NAH (N-acetyl heparosan)

CDS (dermatan sulfate)

6OSCDS (the 6-position of galactosamine residue in dermatan sulfate was sulfated)

All of these sugars can be obtained from Seikagaku Corporation. As the Hep, an article available from the same company as a reagent was used. In this connection, the 2DSH, 6DSH and NDSH were produced using Hep as the material in accordance with the methods described in JP-A-2003-113090 and JP-A-2003-119146.

The Hep, 2DSH, 6DSH and NDSH used herein were analyzed by the "Enzymatic disaccharide analysis by a combination of digestion with a GAG degrading enzyme and high performance liquid chromatography" described in WO 00/06608 (Table 1). In the table, ΔDiHS—OS represents 2-acetamido-2-deoxy-4-O-(4-deoxy-α-L-threo-hex-4-enopyranosyluronic acid)-D-glucose, ΔDiHS—NS represents 2-deoxy-2-sulfamino-4-O-(4-deoxy-α-L-threo-hex-4-enopyranosyluronic acid)-D-glucose, ΔDiHS-6S represents 2-acetamido-2-deoxy-4-O-(4-deoxy-α-L-threo-hex-4-enopyranosyluronic acid)-6-O-sulfo-D-glucose, ΔDiHS-US represents 2-acetamido-2-deoxy-4-β-(4-deoxy-2-O-sulfo-α-L-threo-hex-4-enopyranosyluronic acid)-D-glucose, ΔDiHS-di(6,N)S represents 2-deoxy-2-sulfamino-4-O-(4-deoxy-α-L-threo-hex-4-enopyranosyluronic acid)-6-O-sulfo-D-glucose, ΔDiHS-di(U,N)S represents 2-deoxy-2-sulfamino-4-O-(4-deoxy-2-O-sulfo-α-L-threo-hex-4-enopyranosyluronic acid)-D-glucose, ΔDiHS-di(U,6)S represents 2-acetamido-2-deoxy-4-O-(4-deoxy-2-O-sulfo-α-L-threo-hex-4-enopyranosyluronic acid)-6-O-sulfo-D-glucose and ΔDiHS-tri(U,6,N)S represents 2-deoxy-2-sulfamino-4-O-(4-deoxy-2-O-sulfo-α-L-threo-hex-4-enopyranosyluronic acid)-6-O-sulfo-D-glucose, respectively.

TABLE 1

| Substance name | ΔDiHS- | | | | | | | |
|---|---|---|---|---|---|---|---|---|
| | 0S | NS | 6S | US | di(6,N)S | di(U,N)S | di(U,6)S | tri(U,6,N)S |
| Hep | 3.9 | 2.3 | 3.8 | 1.8 | 11.4 | 6.4 | 1.5 | 68.9 |
| 2DSH | 6.4 | 12.2 | 4.6 | 0 | 76.8 | 0 | 0 | 0 |
| 6DSH | 9.3 | 25.9 | 0 | 6.7 | 4.7 | 53.4 | 0 | 0 |
| NDSH | 3.5 | 0 | 21.8 | 7.1 | 3.1 | 0 | 58.9 | 0 |

Additionally, when their weight average molecular weights were measured by the method described in WO 00/06608, Hep was 14,000, 2DSH was 12,000, 6DSH was 12,500 and NDSH was 11,000.

3. Other Reagent

As FBS, manufactured by EQUITECH-BIO was used.

<2> Methods and Results

1. Actions on Cell Differentiation (1)

Cellular ALP activity was measured as the index of cell differentiation. Cells were inoculated onto a 24 well culture plate at a density of $5 \times 10^3$ cells/well and cultured by adding 50 μg/ml in final concentration of each sample to 2% FBS-containing αMEM. On the first week after the cells reached confluent, ALP activity was measured by the following enzymologic method (Bessey-Lowry method).

Measuring Method of ALP Activity

After washing the cultured cells with PBS, the cells were disrupted and stirred for 40 seconds in 10 mM Tris-HCl buffer (pH 7.4, 500 μl) using an ultra sonic homogenizer (Handy Sonic model UR-20P; mfd. by Tomy Seiko Co., Ltd.). Next, 25 μl of the sample liquid was added to 125 μl of an ALP buffer (0.1M carbonate buffer pH 9.8, 6.7 mM p-nitrophenyl phosphate, 2 mM $MgCl_2$) and incubated at 37° C. for 30 minutes. After terminating the reaction by adding 125 μL of 0.2 N NaOH, the absorbance at 405 nm was measured by using a microplate reader (Model 550, manufactured by Bio-Rad Laboratories). The calculated ALP activity was shown by unit per the number of cells. Additionally, a case in which the sample to be tested was not added was used as a control.

The results in which each sample to be tested was added to the cell strain MC3T3-E1 are shown in FIG. 1, and the results in which a sample to be tested (Hep, 2DSH, 6DSH or NDSH) was added to the cell strain MC3T3-E1 are shown in FIG. 2, and the results in which a sample to be tested (Hep, 2DSH, 6DSH or NDSH) was added to the cell strain ST2 are shown in FIG. 3, respectively.

As shown in FIG. 1 and FIG. 2, each of the Hep, 2DSH, 6DSH and NDSH increased the ALP activity of the cell strain MC3T3-E1. Among them, it was shown that Hep is particularly effective for the increase in ALP activity of the cell strain MC3T3-E1.

Also, as shown in FIG. 3, each of the Hep, 2DSH, 6DSH and NDSH increased the ALP activity of the Cell strain ST2. Among them, it was shown that NDSH is particularly effective for the increase in ALP activity of the cell strain ST2.

From these results, it was shown that all of the Hep, 2DSH, 6DSH and NDSH increase the ALP activity of the bone marrow-derived mesenchymal cell and osteoblast. This indicates that having sulfate groups at two or more positions selected from the group consisting of the 2-, 6- and N-positions in the Hep structure is necessary for the increase in ALP activity of these cells.

It was shown that Hep among them particularly effectively increases the ALP activity of osteoblast, and NDSH particularly effectively increases the ALP activity of the bone marrow-derived mesenchymal cell.

2. Actions on Cell Differentiation (2)

The ALP activity was measured in the same manner, by changing the medium of the aforementioned "Actions on cell differentiation (1)" to a medium which does not contain serum (serum-free medium). The results of adding each sample to be tested (Hep, 2DSH, 6DSH or NDSH) to the cell strain MC3T3-E1 are shown in FIG. 4, and the results of adding each sample to be tested (Hep, 2DSH, 6DSH or NDSH) to the cell strain ST2 are shown in FIG. 5, respectively. In this connection, the calculated ALP activity was shown by a numerical value of cells per DNA weight.

As shown in FIG. 4, all of the Hep, 2DSH, 6DSH and NDSH increased the ALP activity of the cell strain MC3T3-E1 under the serum-free condition. It was shown that Hep, 2DSH and NDSH among them are particularly effective in reinforcing the ALP activity of the cell strain MC3T3-E1.

Also as shown in FIG. 5, all of the Hep, 2DSH, 6DSH and NDSH increased the ALP activity of the cell strain ST2 under the serum-free condition. It was shown that 2DSH among them is particularly effective in reinforcing the ALP activity of the cell strain ST2.

From these results, it was shown that all of the Hep, 2DSH, 6DSH and NDSH increase the ALP activity of the bone marrow-derived mesenchymal cell and osteoblast under a serum-free condition. This indicates that a Hep in two or more positions selected from the group consisting of the 2-, 6- and N-positions in the Hep structure which have the sulfate group has the action to increase ALP activity by directly acting upon these cells without requiring various factors contained in the serum.

It was shown that Hep, 2DSH and NDSH among them particularly effectively increase the ALP activity of osteoblast, and 2DSH particularly effectively increases the ALP activity of the bone marrow-derived mesenchymal cell.

3. Actions on Cell Differentiation (3)

In the aforementioned "Actions on cell differentiation (1)", respective cells were recovered and total RNA was extracted on the first and second weeks after the addition of a sample to be tested, and expression of mRNA of COLI, ALP, osteocalcin, BSP and BMP-2 was analyzed by RT-PCR.

As a result, high induction of ALP mRNA was confirmed in the cell strain ST2 also by the RT-PCR analysis. In the cell strain MC3T3-E 1, induction of COLT and BSP mRNA was also observed in addition to that of ALP.

4. Actions on Cell Differentiation (4)

In order to examine calcification ability of the cells, alizarin staining (ALZ staining; stained in red indicates accelerated calcification) was carried out in accordance with the usual way, in the aforementioned "Actions on cell differentiation (1)" on the first week after the cells reached confluent. The cells were washed with PBS, fixed with 10 neutral-buffered formalin and then stained with 0.01 Alizarin Red S (manufactured by Wako Pure Chemical Industries).

As a result, Hep, 2DSH, 6DSH and NDSH accelerated formation of calcification matter on both of the cell strains ST2 and MC3T3-E1. Particularly on the cell strain ST2, Hep, 2DSH and NDSH showed strong acceleration.

5. Actions on Cell Differentiation (5)

A Wistar rat of 8 weeks of age was subjected to general anesthesia with ethyl carbamate 20 solution at a dose of 0.5 ml per 100 g body weight, and then the forehead skin and periosteum were incised. Each sample to be tested (Hep, 2DSH, 6DSH or NDSH; 100 µl for each) diluted to a concentration of 3 mg/ml with PBS was transplanted under the cranial periosteum. In this case, hydroxyapatite was used as the carrier.

Specifically, a block of hydroxyapatite (size: 3 mm in length×2 mm in breadth×2 mm in height; adsorbs about 0.1 ml of solution) was soaked for 30 minutes in each sample to be tested of a concentration of 3 mg/ml. It was used for the transplantation.

A substance in which test sample-free PBS was used was used as the control.

Each animal was sacrificed on the fourth week and eighth week after transplantation of the sample to be tested. Then slices of the transplanted parts were prepared and subjected to hematoxylin-eosin staining (HE staining). It was observed under an optical microscope to evaluate degree of the formation of a hard tissue (bone).

As a result, only blood vessels and fibrous connective tissues were observed but formation of bone was not observed in the control group. On the other hand, formation of bone was observed in each of the Hep group, 2DSH group, 6DSH group and NDSH group. Remarkable bone formation was found particularly in the 2DSH group.

6. Actions on Cell Differentiation (6)

In the same manner as in the aforementioned "5. Actions on cell differentiation (5)", slices of the transplanted parts were prepared by sacrificing each animal on the fourth week and sixth week after transplantation of the sample to be tested (n=2 for each group). Ratio of the area of formed bone (hard tissue) to the area of the hydroxyapatite region observed in the image of said slice was analyzed by using an image analyzing software (Scion image; Scion Corporation). The results are shown in FIG. 6. In this connection, the gray bar in FIG. 6 shows the results on the fourth week, while the black bar shows the results on the sixth week, respectively.

From FIG. 6, it was shown that formation of bone (hard tissue) was confirmed within a broad range in the Hep group, 2DSH group, 6DSH group and NDSH group, both on the fourth week and sixth week, although it was hardly found in the control group. This effect was remarkable particularly in the 2DSH group and NDSH group.

7. Actions on Cell Differentiation (7)

In the same manner as in the aforementioned "5. Actions on cell differentiation (5)", slices of the transplanted parts were prepared by sacrificing each animal on the fourth week, eighth week and twelfth week after transplantation of the sample to be tested (n=5 for each group). Ratio of the area of bone tissue to the area of the total tissues observed in the image of the slices of transplanted region was analyzed using an image analyzing software (Scion image; Scion Corporation). The results are shown in FIG. 7. In this connection, the bars of respective weeks in FIG. 7 show the results in the control group, 2DSH group, 6DSH group, NDSH group and Hep group, respectively, starting from the left side.

From FIG. 7, although it was shown that formation of bone (hard tissue) was confirmed within a broad range in the Hep group, 2DSH group, 6DSH group and NDSH group, all in the fourth week, eighth week and twelfth week, it was hardly found in the control group. This effect was remarkable particularly in the 2DSH group, Hep group and NDSH group. Since these results are consistent with the results of the "5. Actions on cell differentiation (5)" and "6. Actions on cell differentiation (6)" which were carried out separately and independently, it was shown that they are reproducible.

8. Actions on Cell Growth

Respective cells were inoculated onto a 24 well culture plate (manufactured by Falcon) in $5\times10^3$ cells/well portions. Starting on the first day after the inoculation, each sample to be tested (Hep, 2DSH, 6DSH or NDSH) was added to the culture liquid (αMEM containing 2% FBS) to a final concentration of 50 µg/ml. On the zero day, first day, third day and sixth day after addition of the sample to be tested, the number of cells was counted using a Coulter counter (COULTER Z1, manufactured by Coulter Electronics Inc.). A case in which the sample to be tested was not added was used as the control. The results on the cell strain MC3T3-E1 are shown in FIG. 8, and the results on the cell strain ST2 are shown in FIG. 9. In FIG. 8 and FIG. 9, the axis of abscissa shows the number of days after addition of the sample to be tested, and the axis of ordinate shows the number of cells.

As shown in FIG. 8, although all of the samples to be tested suppressed growth of the cell strain MC3T3-E1, but the growth suppressing effects of 2DSH, 6DSH and NDSH were small in comparison with that of Hep. Additionally, as shown in FIG. 9, although 2DSH accelerated growth of the cell strain ST2, but Hep suppressed it on the contrary.

From these results, it was shown that 2DSH exerts the action to accelerate growth of the bone marrow-derived mesenchymal cell. Also, it was shown that Hep exerts the action to suppress growth of the bone marrow-derived mesenchymal cell.

Additionally it was shown that all of the Hep, 2DSH, 6DSH and NDSH exert the action to suppress growth of the osteoblast.

When the above results were synthetically considered, it was shown that 2DSH and NDSH are particularly effective in increasing the ALP activity in the bone marrow-derived mesenchymal cell and osteoblast and in forming a bone (hard tissue).

9. Preparation Examples

Although preparation examples of the agents of the present invention are shown in the following, these are only examples and dosage forms of the agents of the present invention are not limited thereto.

(1) Ointments

Hep 10 mg

Sorbitan monostearate 7 mg
Polyoxyethylene sorbitan monostearate 7 mg
Isopropyl palmitate 37 mg
Petrolatum 37 mg
Liquid paraffin 37 mg
Cetanol 50 mg
Glycerol 70 mg
Magnesium stearate 2 mg By adding purified water to the above components, 1 g of a cream was prepared.

(2) Tablets
2DSH 100 mg
Lactose 670 mg
Potato starch 150 mg
Crystalline cellulose 60 mg
Light anhydrous silicic acid 50 mg After mixing the above components, a solution prepared by dissolving 30 mg of hydroxypropylcellulose in methanol (10% by weight of hydroxypropylcellulose) was added thereto, and the resulting mixture was kneaded and granulated. It was made into granular forms by extruding through a 0.8 mm screen. After drying, it was mixed with 15 mg of magnesium stearate and then 200 mg by 200 mg of it was subjected to tablet making to obtain tablets.

(3) Capsules
6DSH 100 mg
Lactose 80 mg

The above components were uniformly mixed and filled in a hard capsule to obtain capsules.

(4) Injections
NDSH 30 mg

The above component was dissolved in 2 ml of 5% mannitol aqueous solution. It was subjected to aseptic filtration and then put into an ampoule and sealed.

(5) Injections for Dissolution when Used
(A) 2DSH (freeze-dried) 30 mg (enclosed in an ampoule)
(B) Aseptically filtered PBS 2 ml (enclosed in an ampoule)

Using the above (A) and (B) as one set, injections for dissolution when used were produced. When used, (A) can be used by dissolving it in (B).

In this connection, the active ingredients of the agents of the present invention showed no particular changes when conditions of the cells and animals were observed every day in the aforementioned drug effect pharmacological tests. Based on this, safety of the agents of the present invention can be sufficiently estimated.

While the present invention has been describe in detail and with reference to specific embodiments thereof, it will be apparent to one skilled in the art that various changes and modifications can be made therein without departing from the spirit and scope of the present invention.

This application is based on a Japanese patent application filed on Mar. 14, 2005 (Japanese Patent Application No. 2005-071023) and a Japanese patent application filed on Jun. 16, 2005 (Japanese Patent Application No. 2005-176311), and the contents thereof are incorporated by reference. All of the references cited herein are incorporated as a whole.

Industrial Applicability

The agents of the present invention can be used as medicines, reagents and the like with the purpose of accelerating hard tissue formation, accelerating differentiation of cells and reinforcing ALP activity of cells.

BRIEF DESCRIPTION OF THE DRAWINGS

FIG. 9 is a graph showing influence upon the growth of ST2 cell.

Figure 1:
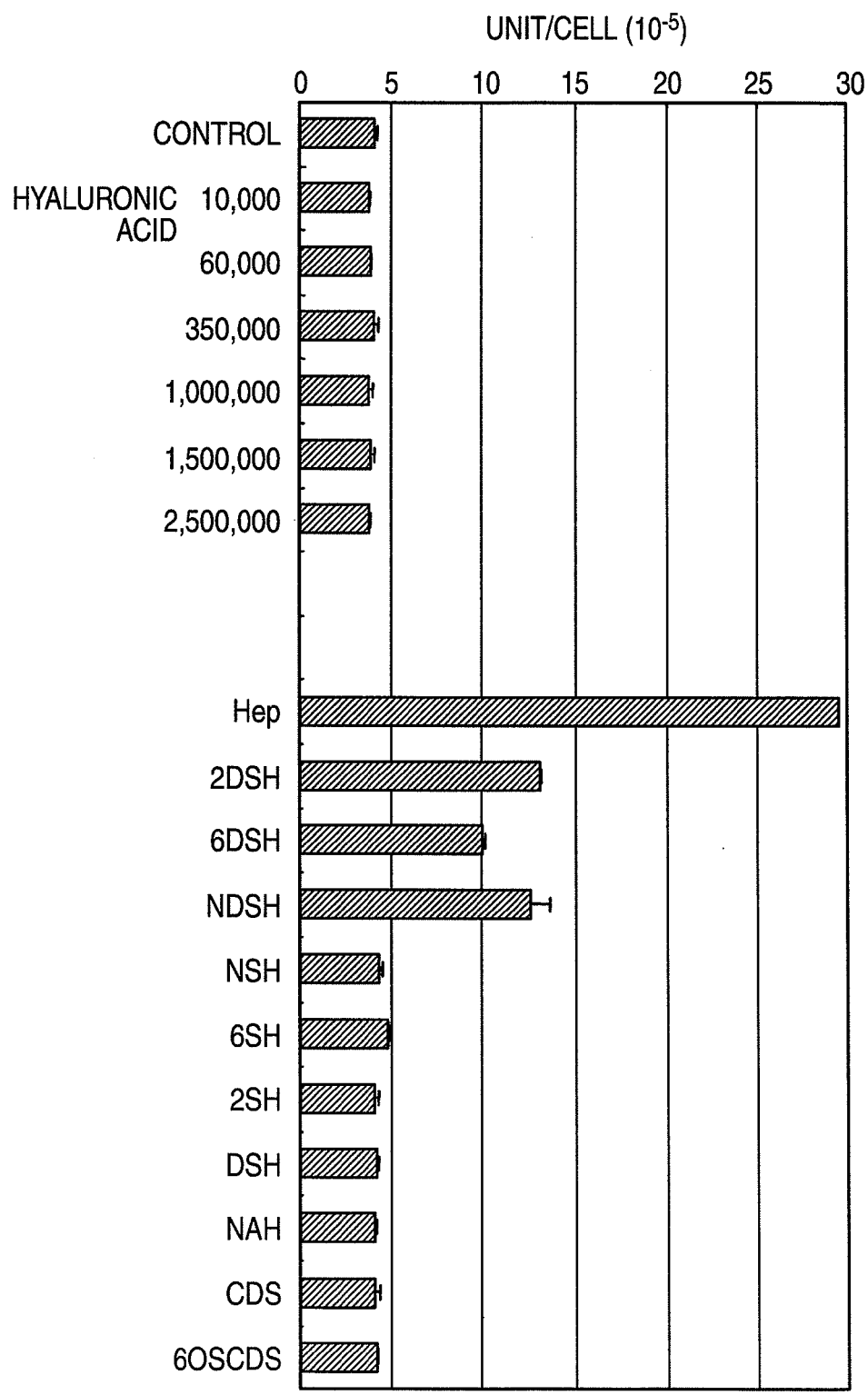
FIG. 1 is a graph showing increase in ALP activity in MC3T3-E1 cell.
Figure 2:
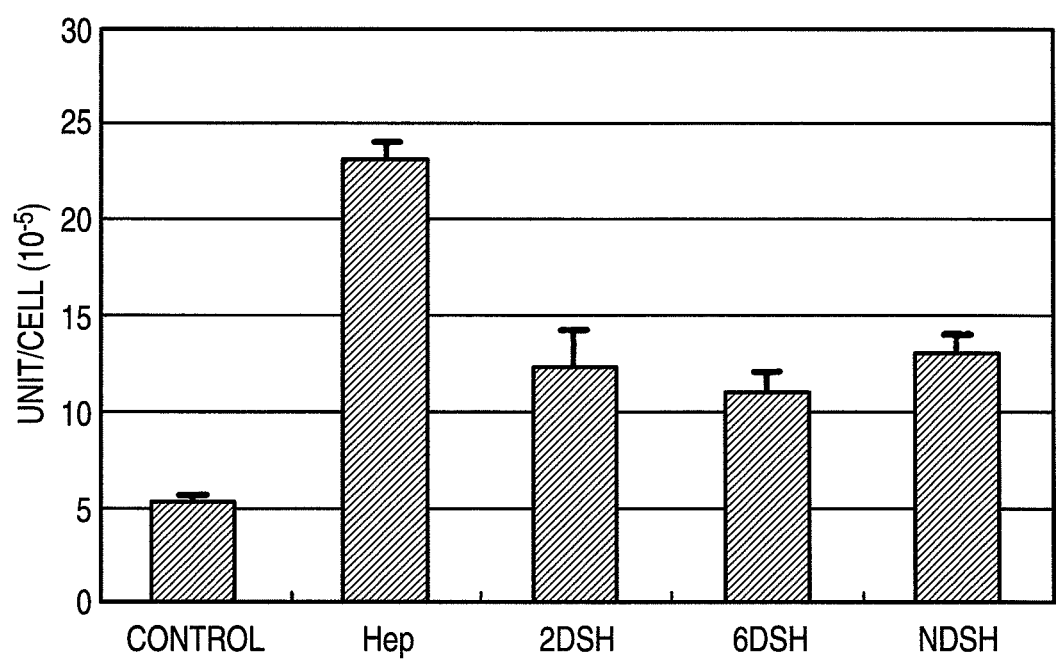
FIG. 2 is a graph showing increase in ALP activity in MC3T3-E1 cell.
Figure 3:
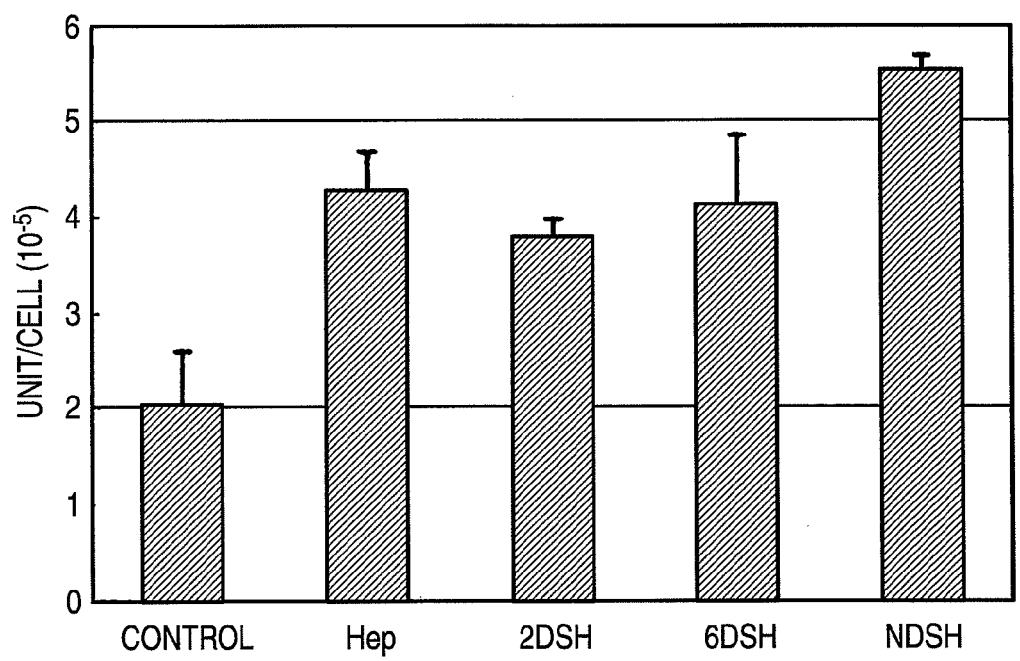
FIG. 3 is a graph showing increase in ALP activity in ST2 cell.
Figure 4:
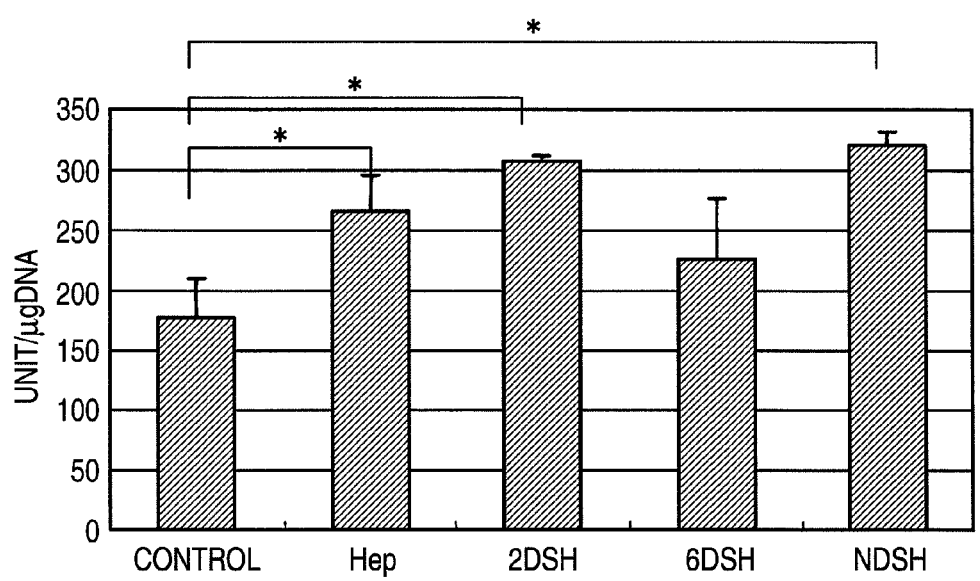
FIG. 4 is a graph showing increase in ALP activity in MC3T3-E1 cell under serum-free condition.
Figure 5:
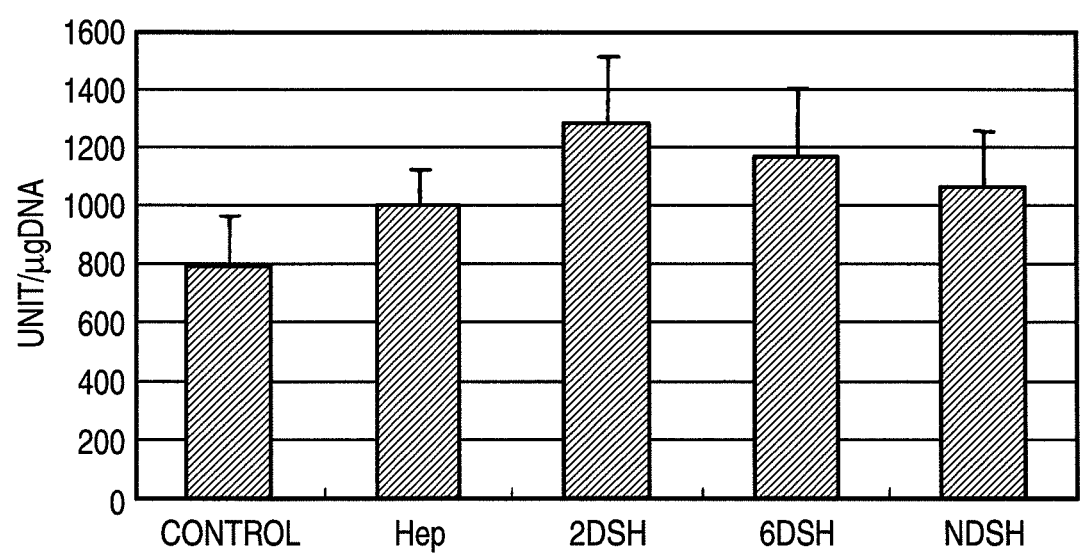
FIG. 5 is a graph showing increase in ALP activity in ST2 cell under serum-free condition.
Figure 6:
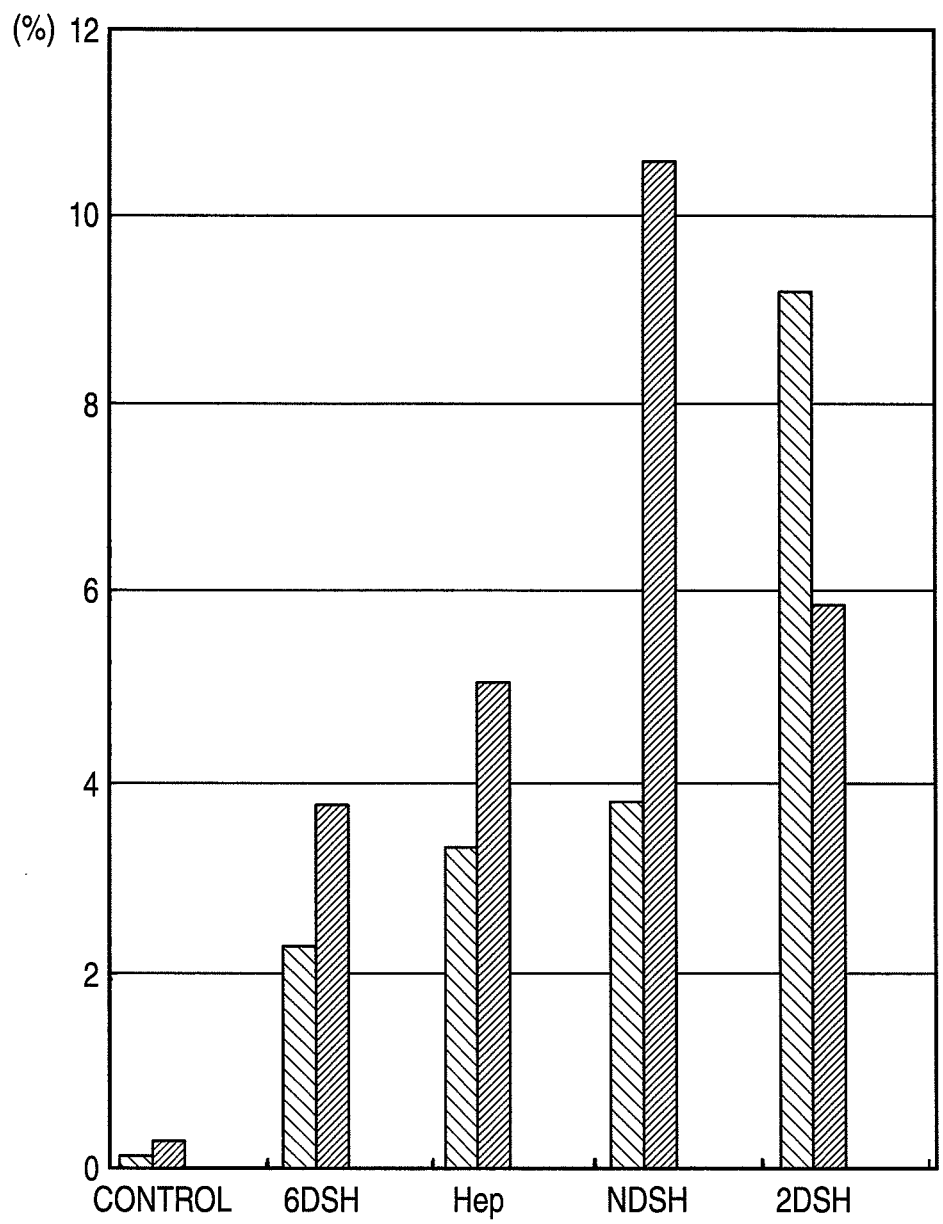
FIG. 6 is a graph showing ratio of the area of a region where a bone (hard tissue) was formed.
Figure 7:
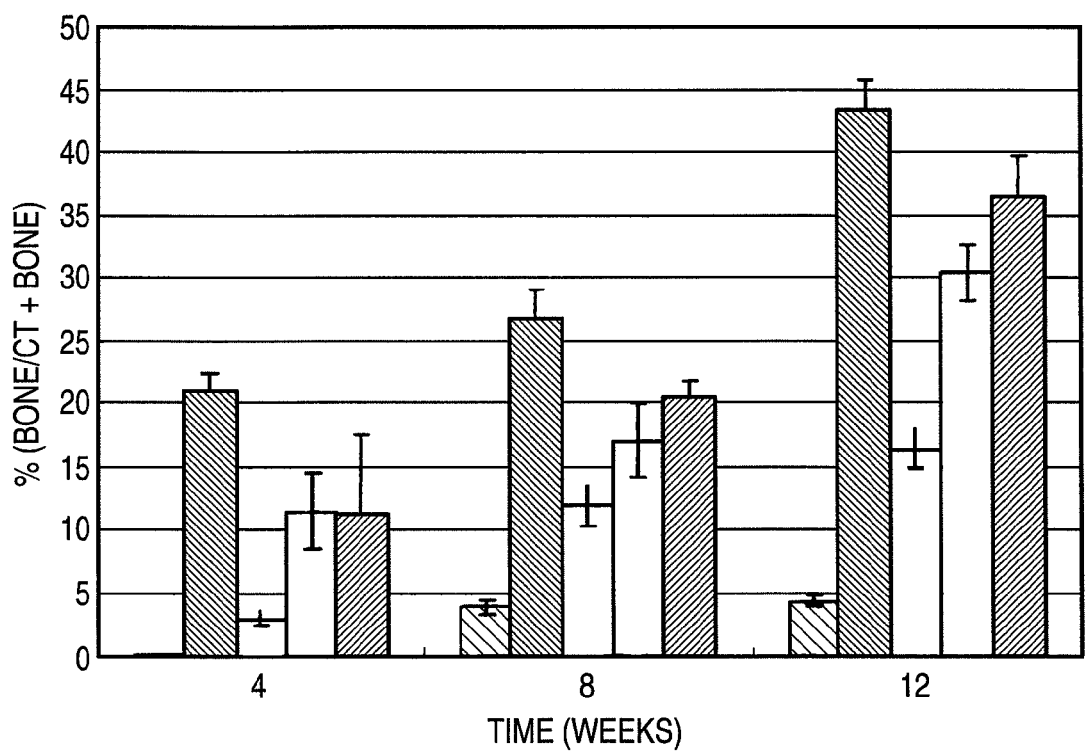
FIG. 7 is a graph showing ratio of the area of a region where a bone (hard tissue) was formed.
Figure 8:
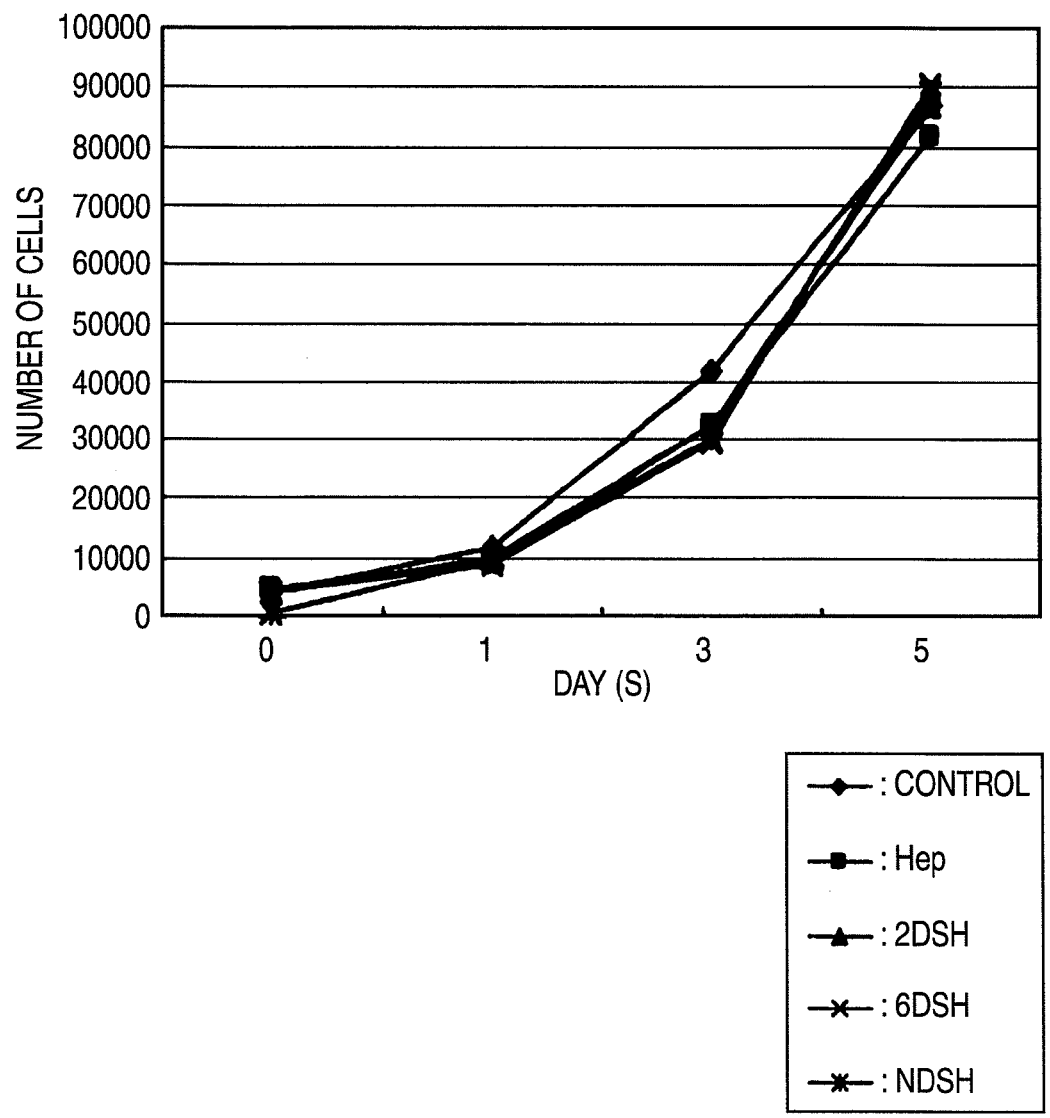
FIG. 8 is a graph showing influence upon the growth of MC3T3-E1 cell.

The invention claimed is:

1. A method of accelerating differentiation in a cell, said method comprising administering to an isolated bone marrow-derived mesenchymal cell a cell differentiation promoter comprising, as an active ingredient, a partially desulfated heparin or a salt thereof in an amount effective to directly act on the cell to accelerate differentiation of the cell, said partially desulfated heparin having a sulfate group and is selected from the group consisting of a substance which does not have the sulfate group on the 2-position hydroxyl group of the hexuronic acid residue of a heparin, a substance which does not have the sulfate group on the 2-position amino group of the glucosamine residue of a heparin, and a mixture thereof.

2. The method of claim 1, wherein the cell differentiation promoter further comprises a carrier.

3. The method of claim 1, wherein the cell differentiation promoter increases alkaline phosphatase activity of the cell.

4. The method of claim 1, wherein the desulfated heparin has sulfate groups at two positions selected from the group consisting of the 2-position, the 6-position, and the N-position of a Hep structure.

* * * * *